(12) United States Patent
Tillotson et al.

(10) Patent No.: US 7,530,266 B2
(45) Date of Patent: May 12, 2009

(54) ACOUSTIC PROFILER FOR WIND, TEMPERATURE, AND TURBULENCE

(75) Inventors: Brian J. Tillotson, Kent, WA (US); Bronwyn A. Jackson, Seattle, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 12/039,987

(22) Filed: Feb. 29, 2008

(65) Prior Publication Data

US 2008/0148839 A1 Jun. 26, 2008

Related U.S. Application Data

(62) Division of application No. 11/381,506, filed on May 3, 2006, now Pat. No. 7,343,793.

(51) Int. Cl.
*G01W 1/00* (2006.01)
(52) U.S. Cl. .................................................. 73/170.16
(58) Field of Classification Search .............. 73/170.17, 73/170.16
See application file for complete search history.

(56) References Cited

U.S. PATENT DOCUMENTS

| 4,995,011 | A | 2/1991 | Spiesberger | |
|---|---|---|---|---|
| 6,480,142 | B1 * | 11/2002 | Rubin | 342/26 R |
| 6,700,834 | B2 * | 3/2004 | Brumley et al. | 367/90 |
| 2002/0018400 | A1 * | 2/2002 | Brumley et al. | 367/90 |
| 2004/0184350 | A1 * | 9/2004 | Brumley et al. | 367/90 |

OTHER PUBLICATIONS

Le Pichon Alex, et al., "Acoustic propagation and atmosphere characteristics derived form infrasonic waves generated by the Concorde", Journal of the Acousitcal Sociatey of America, AIP?Acoustical Society of America, Melville, NY, US, vol. 111, No. 1, Jan. 1, 2002, pp. 629-641, XP012002722, ISSN: 0001-4966.

Balachandran, N K et al, "Concorde sonic booms as an atmospheric probe", Science USA, vo. 197, No. 4298, Jul. 1, 1977, pp. 47-49, XP002480442, ISSN: 0036-8075.

(Continued)

*Primary Examiner*—Andre J Allen
(74) *Attorney, Agent, or Firm*—Felix L. Fischer

(57) ABSTRACT

Characterizing atmospheric conditions is accomplished by measuring at least one varying spectral characteristic of sound at a plurality of intervals from a sound source with the point of measurement and the sound source in relative motion and separated by altitude. The spectral characteristic of the sound at each interval is attributed to a path traveled by the sound and a plurality of simultaneous equations is created for the plurality of paths using a second plurality of altitude segments for each path, each segment having a particular vector as a variable on the spectral characteristic, the initial coefficients in each vector assumed based on predetermined atmospheric models for each altitude segment. The resulting calculated vector and the predetermined atmospheric model are iterated for a minimized cost function in a variational analysis to determine the vector for each altitude segment, the vector providing atmospheric properties for the associated altitude segment.

6 Claims, 15 Drawing Sheets

OTHER PUBLICATIONS

Wilson, D K. et al, "An overview of acoustic travel-time tomography in the atmosphere and its potential applications" Acustica—Acta Acustica S. Hirzel Verlag Germany, vol. 87, No. 6, Nov. 2001, pp. 721-730, XP002480444 ISSN: 1436-7947.

Ostashev, V E et al, "Acoustic tomography of the atmosphere", Geoscicence and Remote Sensing Symposium, 2000, Proceedings, IGARSS 200 0. IEEE 2000 International Jul. 24-28, 2000, Piscataway NJ, USA, IEEE, vol. 3, Jul. 24, 2000, pp. 1186-1188, XP010502919, ISBN: 978-0-7803-6359-5.

Arnold, K et al, "Tomographic monitoring of wind and termperature at different heights above the ground", Acustica—Acta Acustica S. Hirzel Verlag Germany, vol. 87, No. 6, Nov. 2001, pp. 703-708, XP002480443, ISSN: 1436-7947.

* cited by examiner

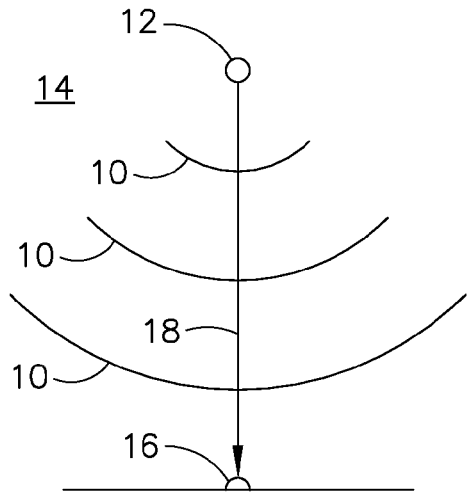
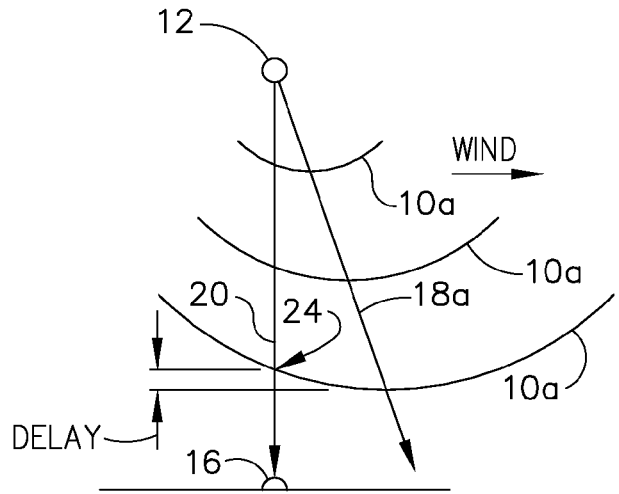
FIG. 1a    FIG. 1b
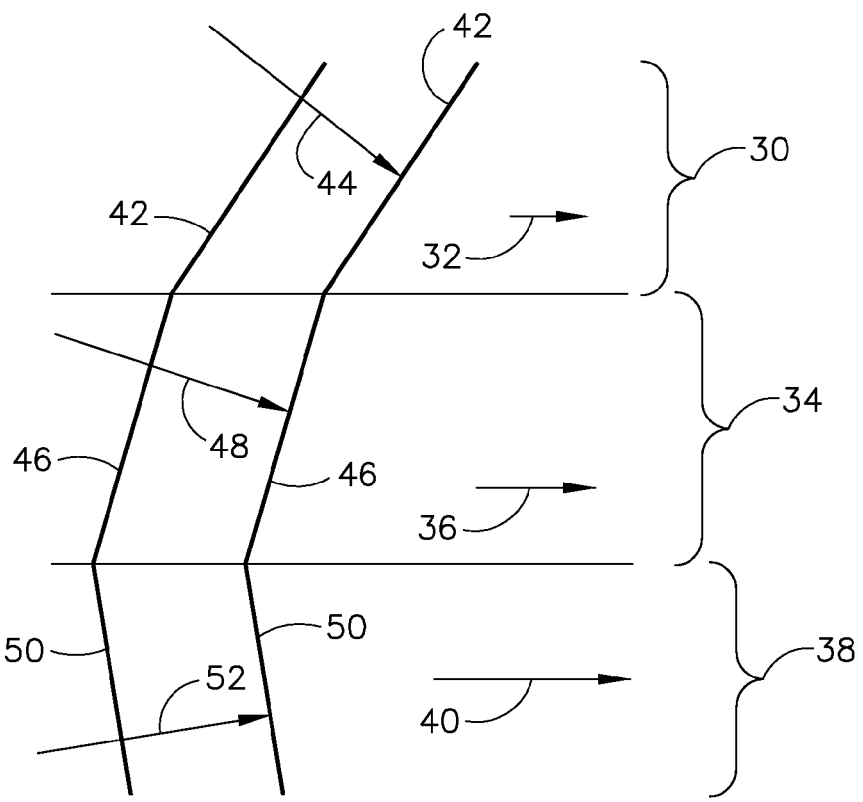
FIG. 1c $$(Hx-y_0)^T \overbrace{\begin{pmatrix} \Delta f_0 \\ \Delta f_1 \\ \Delta f_2 \\ \Delta f_3 \\ \Delta f_4 \end{pmatrix}}  \overbrace{\begin{pmatrix} 9 & 0 & 0 & 0 & 0 \\ 0 & 8 & 0 & 0 & 0 \\ 0 & 0 & 6 & 0 & 0 \\ 0 & 0 & 0 & 4 & 0 \\ 0 & 0 & 0 & 0 & 2 \end{pmatrix}}^{R} \overbrace{(\Delta f_0\ \Delta f_1\ \Delta f_2\ \Delta f_3\ \Delta f_4)}^{Hx-y_0}$$

FIG. 8a $$(Hx-y_0)^T \overbrace{\begin{pmatrix} \Delta f_0 \\ \Delta f_1 \\ \Delta f_2 \\ \Delta f_3 \\ \Delta f_4 \\ \Delta A_0 \\ \Delta A_1 \\ \Delta A_2 \\ \Delta A_3 \\ \Delta A_4 \end{pmatrix}} \overbrace{\left(\begin{array}{ccccc|ccccc} 9 & 0 & 0 & 0 & 0 & 0 & 0 & 0 & 0 & 0 \\ 0 & 8 & 0 & 0 & 0 & 0 & 0 & 0 & 0 & 0 \\ 0 & 0 & 6 & 0 & 0 & 0 & 0 & 0 & 0 & 0 \\ 0 & 0 & 0 & 4 & 0 & 0 & 0 & 0 & 0 & 0 \\ 0 & 0 & 0 & 0 & 2 & 0 & 0 & 0 & 0 & 0 \\ \hline 0 & 0 & 0 & 0 & 0 & 3 & 0 & 0 & 0 & 0 \\ 0 & 0 & 0 & 0 & 0 & 0 & 3 & 0 & 0 & 0 \\ 0 & 0 & 0 & 0 & 0 & 0 & 0 & 3 & 0 & 0 \\ 0 & 0 & 0 & 0 & 0 & 0 & 0 & 0 & 2 & 0 \\ 0 & 0 & 0 & 0 & 0 & 0 & 0 & 0 & 0 & 1 \end{array}\right)}^{R} \overbrace{(\Delta f_0\ \Delta f_1\ \Delta f_2\ \Delta f_3\ \Delta f_4\ \Delta A_0\ \Delta A_1\ \Delta A_2\ \Delta A_3\ \Delta A_4)}^{Hx-y_0}$$

ACOUSTIC PROFILER FOR WIND, TEMPERATURE, AND TURBULENCE

REFERENCE TO RELATED APPLICATIONS

The present application is a divisional application of U.S. application Ser. No. 11/381,506 filed on May 3, 2006 having the same title as the present application, the disclosure of which is fully incorporated herein by reference.

BACKGROUND OF THE INVENTION

1. Field of the Invention

The present invention relates to atmospheric modeling and prediction and more particularly to a system and method employing acoustic sensing for profiling wind, temperature and turbulence.

2. Description of the Related Art

Currently, one of the biggest gaps in global weather monitoring, and therefore in the ability to predict weather, is wind data. Satellites do fairly well at temperature and water vapor content, but can only estimate winds by tracking clouds in photographs. This does not work in clear weather and it does not reveal winds below a cloud deck. Balloon-borne radiosondes measure winds aloft quite well, but only near the places where they are launched, and (usually) only twice a day.

The most useful form of wind monitoring would cover many locations, provide wind speed and direction at all altitudes above each location, and provide the information frequently. Because large transport planes routinely fly over much of the globe, they are a potentially useful tool for making such measurements. Some proposals call for equipping airliners with Doppler lidar or radar capable of measuring winds at many altitudes, even in clear air. However, commercial aircraft operators may be unwilling to accept the cost in weight, power, volume, maintenance, and supplemental FAA certification for carrying lidar or modifying radar.

An alternative is to place ground-based radar wind profilers such as Next Generation Weather Radar (NEXRAD) at many locations. The National Oceanic and Atmospheric Administration (NOAA) has deployed some of these within the US. Regrettably, these profilers are expensive and quite large. Because they are expensive, they are deployed sparsely, so there are important gaps in coverage, e.g. mountainous regions of the US. Because they are also large, they are unsuited to installation on the buoys currently deployed by NOAA at several locations in the oceans. Therefore, weather buoys measure only surface winds, not the higher altitude winds that drive weather.

Another alternative is to place Sound Detection and Ranging (SODAR) profilers at many locations. These devices emit a loud pulse of sound, then measure the weak signal scattered backward by air. The amplitude and Doppler shift of the return signal can reveal winds. The altitude range of SODAR is less than a kilometer as demonstrated by data provided at http://www.sodar.com/about_sodar.htm. Though smaller and cheaper than NEXRAD, the devices are still too large and costly for widespread deployment or for use on buoys. SODAR devices also lead to complaints by people living nearby, since the sound pulse is audible. A related technology is acoustic tomography using time of flight from pulsed active emitters to an array of microphones. This has been used by some foreign groups to estimate winds within a few hundred meters of the ground (see K. Arnold, A. Ziemann, A. Raabe, "Tomographic Monitoring of Wind and Temperature at Different Heights Above the Ground", acta acustica, Vol. 87 (2001) 703-708), but this method has the same altitude limitations as SODAR.

Another alternative is to launch more radiosondes (weather balloons). These typically get good wind and temperature measurements from the surface to the top of the troposphere. However, each is used only once, so using more of them would increase the $36 million the National Weather Service already spends each year on radiosondes. The cost is increased more if the radiosondes must be released from ships to get ocean coverage: ship operations cost so much that NOAA recently stopped funding a meteorology ship in the North Pacific, even though this action strongly reduced the quality of forecasts on the US west coast.

It is therefore desirable to provide an affordable way to gather frequent wind vector data over oceans or other remote areas without large payloads on aircraft or buoys.

It is also desirable to provide a means for detecting turbulence. Turbulence refers to localized wind variations that are not part of large-scale movement of bodies of air. Turbulence is notoriously hard to detect in clear air aside from direct flight encounters by aircraft. Existing methods mostly have short range in clear air, and are therefore used only near airports where wind shear is a hazard. It is desirable to provide a solution for detecting turbulence over larger areas.

SUMMARY OF THE INVENTION

The present invention provides a method for characterizing atmospheric conditions by measuring a varying spectral characteristic of sound at a plurality of intervals from a sound source with the point of measurement and the sound source in relative motion and separated by altitude; in an exemplary embodiment using a ground based microphone to detect sound from an aircraft passing overhead. The spectral characteristic of the sound at each interval is attributed to a path traveled by the sound. A set of simultaneous equations is created for the path at each interval using multiple altitude segments for each path, each segment having a particular vector as a variable on the spectral characteristic. The initial coefficients in each vector are assumed based on predetermined atmospheric models for the associated altitude segment. The resulting calculated vector and the predetermined atmospheric model are iterated to obtain a minimized cost function in a variance analysis to determine the vector for each altitude segment. The vector provides atmospheric properties such as wind speed and direction and temperature for the associated altitude segment.

In various embodiments of the invention, the spectral characteristic measured is arrival time, sound frequency, sound attenuation or the arrival angle. Additionally, by identifying rapidly changing spectral characteristics within one path as identifying turbulence, a plurality of actual paths is calculated based on the vectors and the position of the turbulent region in the actual paths is identified based on the calculated locations of the rapidly changing spectral characteristic.

An exemplary embodiment of a system for characterizing atmospheric conditions according to the present invention provides means for recording acoustic spectral characteristics of sound from an over flying airplane. A computer processor is then employed for analyzing the acoustic spectral characteristics recorded during the airplane overflight and the evolution of the spectral characteristics over time during the overflight. The computer system then relates the evolution of spectral characteristics to determine the most probable distribution of wind and temperature as functions of altitude.

As additional elements of the system, a transmission system reports the flight data of the aircraft sound source including a vector difference of true airspeed and true groundspeed of the airplane for applying the vector difference as a windspeed upper boundary condition in developing the most probable distribution.

The simple components in the measurement system employed by the present invention to measure acoustic data from overflying aircraft as available sources provide an affordable way to gather frequent wind vector data over remote areas without large payloads on aircraft or buoys or complex ground stations.

Additionally, with enhanced data analysis conducted within the existing components of the system, detection and location of turbulence is achieved and can be applied over large areas.

These and other features and advantages of the present invention will be better understood by reference to the following detailed description when considered in connection with the accompanying drawings.

BRIEF DESCRIPTION OF THE DRAWINGS

FIG. 1a is a schematic view of sound waves arriving along a vertical path in calm air through the atmosphere to a microphone;

FIG. 1b is a schematic view of sound waves arriving at a microphone after displacement by the wind;

FIG. 1c is a schematic view of sound wave front refraction in various layers of the atmosphere and the resulting directional vectors of the sound;

FIG. 4b is a graph of frequency vs. sound arrival times with reference to emission times for the two microphones of FIG. 4a;

FIG. 8a is an exemplary matrix calculation demonstrating weighting matrix R for calculation of forward model H; and, FIG. 8b is a second exemplary matrix calculation demonstrating weighting matrix R for calculation of forward model H.

DETAILED DESCRIPTION OF THE INVENTION

Figure 2A:
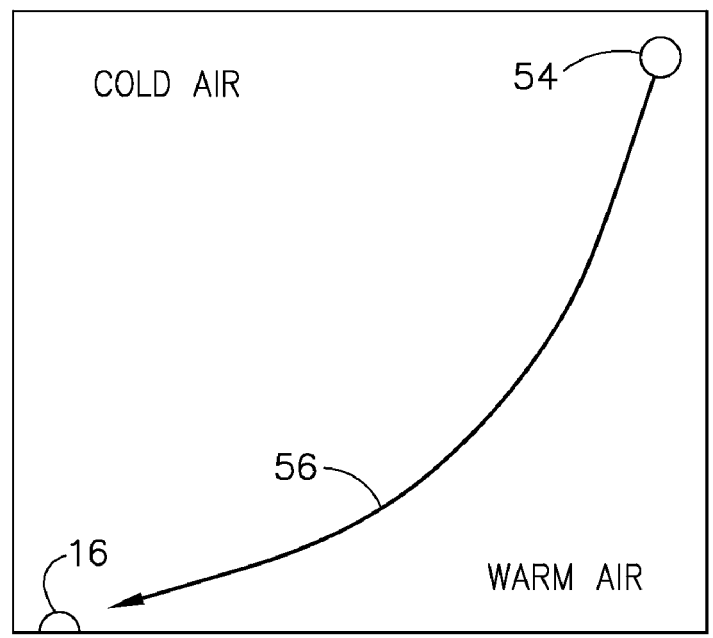
FIG. 2a is a schematic view of the curved path followed by a sound emitted from a source at altitude to a microphone on the ground.

The invention exploits the relationship between sound waves, wind shear, and temperature. In still air, sound emitted directly above a surface-based microphone will travel in a straight line from the sound source to the microphone. FIG. 1a demonstrates physical phenomenon with sound waves 10 emitted from a source 12 traveling through atmosphere 14 to a receiver (microphone) 16. The straight path of the sound waves is represented by vector 18. The time for the sound to arrive at the ground is determined by the emitter's altitude and by the temperature at each altitude between the emitter and the ground. The relationship between temperature and sound velocity will be discussed in greater detail subsequently.

When wind blows, the sound waves are carried along with the air. As shown in FIG. 1b, in the case of sound traveling straight down along a vector 20 through a horizontal wind, which displaces the waves along vector 18a the part of the wavefront that reaches the microphone must travel a slanting path 24 (relative to the moving air) which is perpendicular to the incident wave front 10a. The time of arrival is delayed by an amount 26 compared to the case with no wind. This delay is a relative measure of mean wind speed between the emitter and the receiver.

For non-vertical sound paths and winds that vary with altitude, the situation is more complicated. A wind gradient can bend acoustic wave fronts. Sound that follows a non-vertical path is refracted as it traverses a vertical wind gradient. Acoustic wave fronts moving from top layer to bottom layer encounter wind shear. This phenomenon is shown in FIG. 1c wherein a first or top layer 30 has a wind velocity represented by vector 32. A second or middle layer 34 has a wind velocity represented by vector 36 which has a higher magnitude (greater velocity) than the first layer. This carries wave fronts forward faster than in top layer. The wavefront therefore bends, changing the direction of sound. The wave fronts 42 in the first layer have a motion represented by vector 44 while the wave fronts 46 from the same emitted sound in the second layer have a motion represented by vector 48 and, similarly, in a third or bottom layer 38 with a wind velocity represented by vector 40, third layer wave fronts 50 have a motion represented by vector 52. This refraction also affects the time of arrival at a receiver on the ground. If the gradient is strong enough, sound can refract so much that it travels upward as shown in the bottom layer of FIG. 1c.

The wind speeds are resolvable at various altitudes by considering the usual variation of temperature vs. altitude, i.e. the adiabatic lapse rate of about 2 degrees C. per thousand feet of altitude gained. Under normal conditions, lower altitudes have warmer temperature as represented in FIG. 2a. The speed of sound is proportional to the square root of absolute temperature. This means the speed of sound is greater at low altitude, so a sound wave coming down at a non-vertical angle in still air will be refracted farther from the vertical.

Figure 2B:
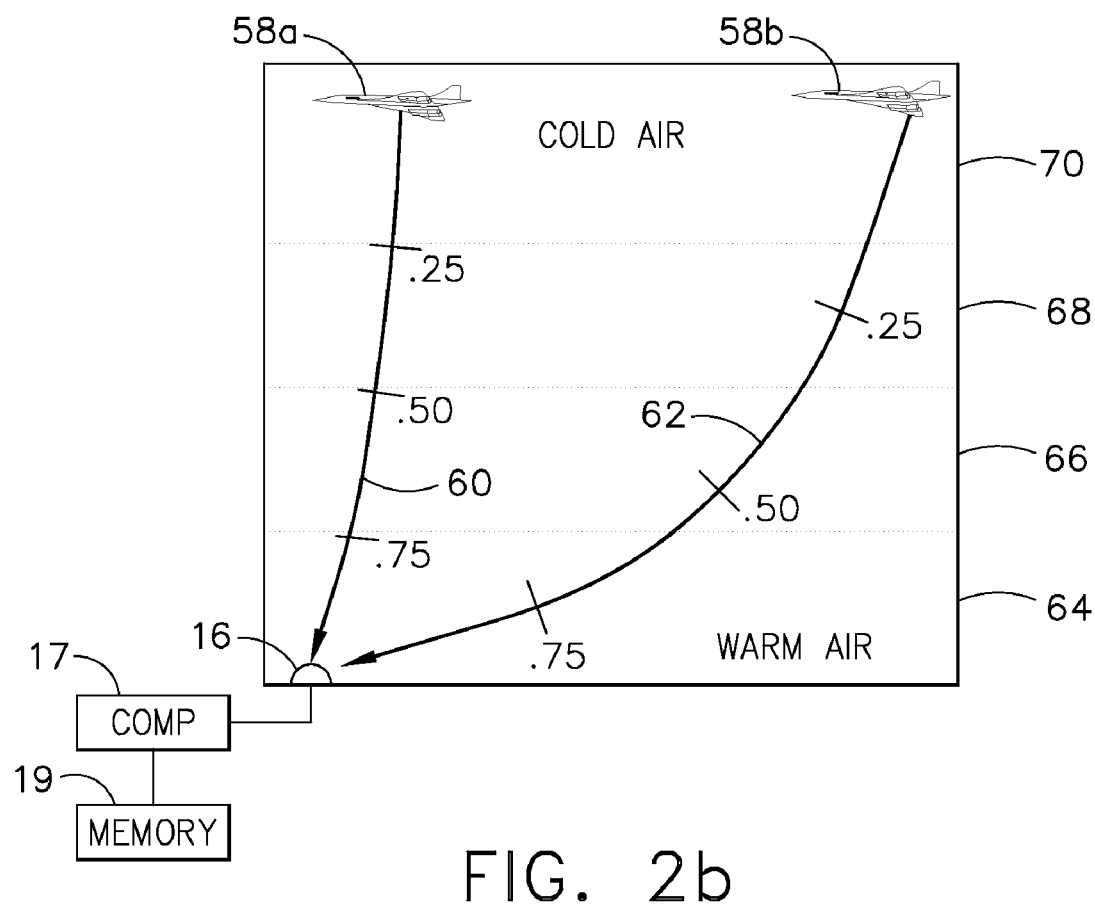
FIG. 2b is a schematic view showing different curvature of sound paths propagating from a source transitioning from a position away from the microphone toward a zenith over the microphone.

As shown in FIG. 2a, wavefronts of sound from a source 54 moving at non-vertical angle represented generally by the line 56 are bent away from vertical by temperature gradient. In FIG. 2b, sound coming from a first source 58a will follow a path 60 while sound from a second source 58b (or the same source at a different time) at the same altitude but farther away spends larger percentage of its path 62 at lower altitude. (All curvatures exaggerated for clarity.)

With an airplane as the sound source, the consequence of this bent path is that sound waves coming from an airplane far away spend relatively more of their time in low-altitude air, while sound waves from an airplane overhead spend relatively more of their time in high-altitude air. Refraction also limits the range of acoustic detection for airplanes. If the airplane is sufficiently far away in horizontal distance, its sound is totally refracted upward and does not reach the microphone on the surface. Thus, low-altitude delays have relatively more effect on sound from an airplane far away, while high-altitude delays have relatively more effect on sound from an airplane near the zenith.

Applying a method in accordance with the present invention, when an airplane overflies microphone 16, collection of many acoustic samples is accomplished using a computerized data acqusition system 17 having a memory 19 for storage of modeled data, as will be described subsequently, each sample giving slightly different statistical significance to delays at various altitudes. By solving a set of simultaneous equations, values proportional to the delays incurred at each altitude are identified providing an estimate of the winds and temperatures at each altitude. It is assumed for purposes of simplicity in the embodiments discussed herein that the winds only deflect the sound a small distance from its nominal path. Very strong winds cause large deflections and must be analyzed by non-linear methods.

Figures 3A, 3B:
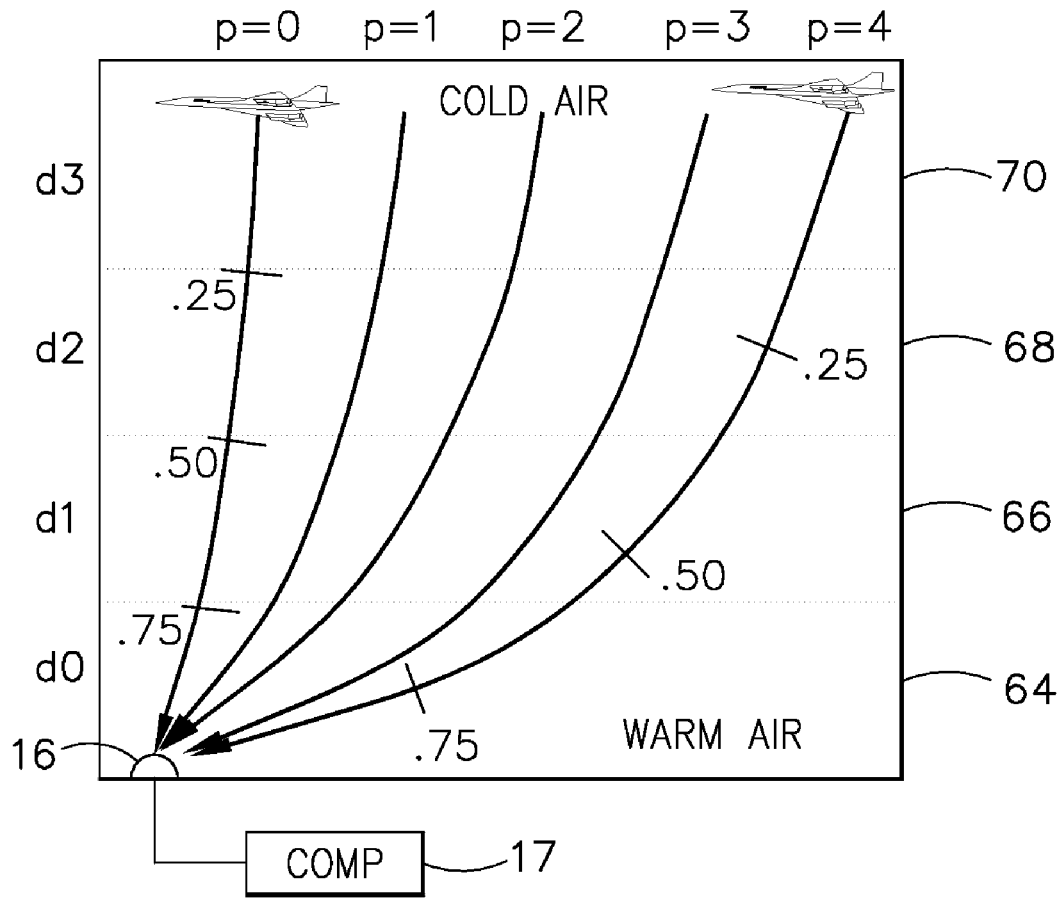
FIG. 3a is a schematic view of multiple curved sound paths with relative distances traveled in each of a number of designated layers of the atmosphere.
FIG. 3b is a matrix equation representing the simultaneous equations relating a measured characteristic of the paths, S, to a variable, D, at each layer of the atmosphere using modeled coefficients of atmospheric properties A.

FIG. 3a shows graphic representation of the sound paths through the atmosphere for four of the acoustic samples taken with the aircraft at various ranges and FIG. 3b shows in matrix form a simplified set of simultaneous equations that model these samples. The values $d_i$, are the reciprocal of the speed at which the sound travels for each of the four layers or altitude bins 64, 66, 68 and 70 shown in FIGS. 2b and 3a. The reciprocal of the speed at which the sound travels in each layer, including the effect of wind is represented by matrix D. As an example of one potential measurement, the total shift, $s_j$, in arrival time for sound traversing each path, p, is measured with the acoustic samples. This set of measurements is represented by matrix S. The relative effect created by the reciprocal of the speed of the sound, $d_i$ on each path shift $s_p$ is represented by matrix A. As the notional values show, low altitude speed of sound effects (d0) attributable to layer 64 have more effect on shifted arrival times of the longest path (p=4) than for the shorter paths. Matrix A values are proportional to the distance sound travels while following each path (p=0.4) through each layer. Values in S are the travel times along each path. Thus, units of D are sec/meter, units of A are meters, and units of S are seconds of travel time along each path.

Given the measured arrival time shifts, S, matrix A is inverted and employed to solve the simultaneous equations for the relative speeds of the sounds, D. (The case shown is overdetermined based on the availability of a larger number of equations than variables, allowing the use of statistical methods to get robust estimates for the $d_i$ values.) From the values of D, the winds are computed.

Measured values of S are used with an initial estimate of A to compute D. D values include the effect of wind, which distorts path shapes and therefore affects A. Thus, a high-precision estimate of winds and temperatures may require iterating estimates of A and D until the solution converges.

The assumptions discussed for the models above imply any wind will delay the arrival of sound waves. However, for sound waves that do not travel vertically, horizontal winds can either delay or accelerate the sound's arrival, depending on the direction of the wind. Winds aligned with the airplane's path will make sound arrive later while the airplane approaches, but will make it arrive earlier while the airplane is getting farther away if the wind is blowing opposite to the aircraft's velocity as represented in FIG. 3f wherein the relative "path length" 63d is shorter than 63f, or the opposite effect if the wind is blowing in the same direction as the aircraft is traveling. Winds perpendicular to the airplane's path will delay all sounds if they blow from the microphone toward the airplane's ground track, but will accelerate some sounds if they blow from the ground track toward the microphone. Though complicated, all these contributions to the arrival time can be disambiguated by solving a set of simultaneous equations with appropriate weights for each altitude. Alternatively, a measured pattern of arrival times can be used to find a best-fit with predictions made by computer models using various combinations of winds and temperatures.

Figure 3C:
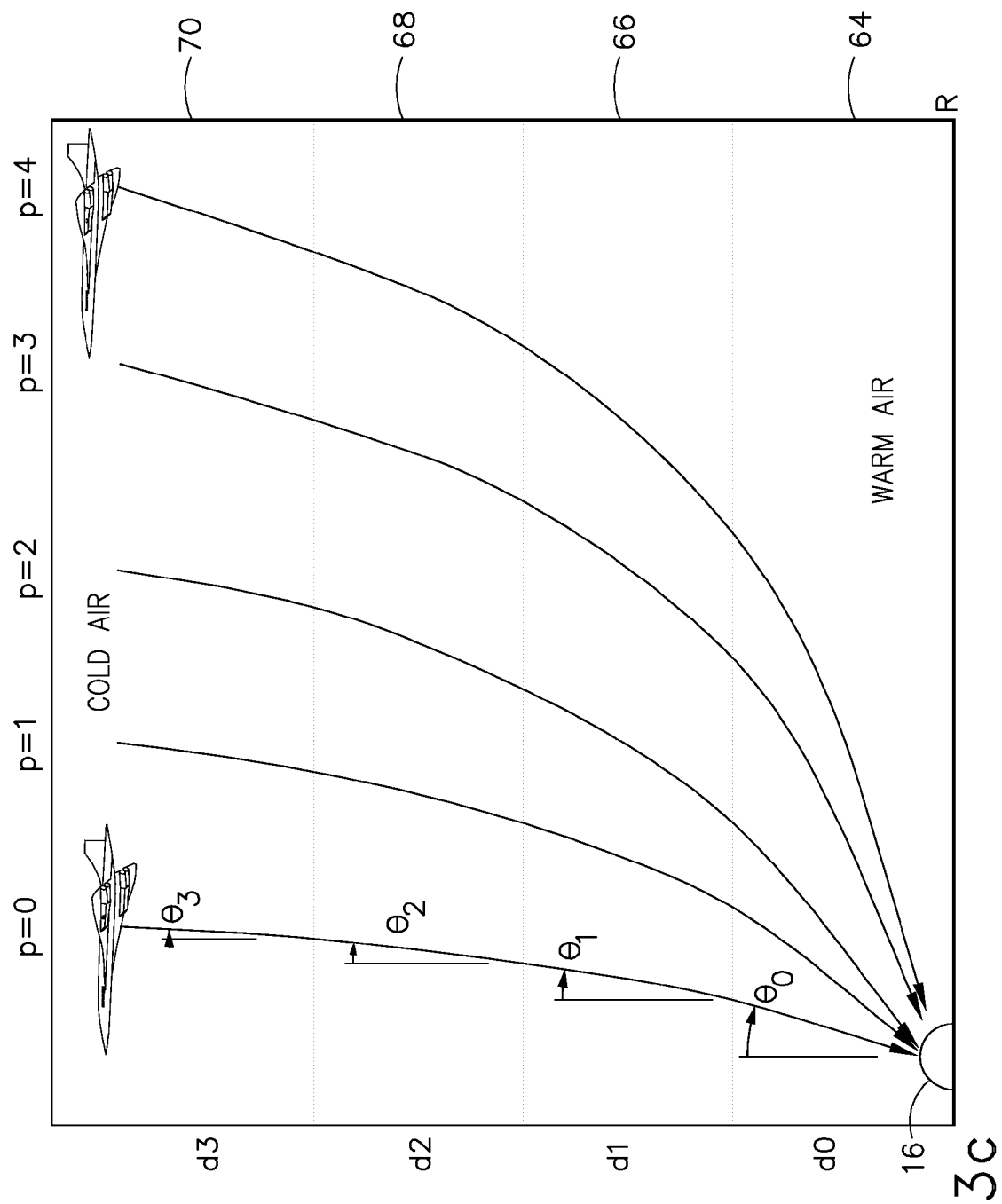
FIG. 3c is a detailed view of the angles of the sound path in each of the atmosphere layers.

Matrix A values, as shown in exemplary form in FIG. 3b, are the distance sound travels while following each path (p=0.4) through each layer, 64, 66, 68 and 70 having a corresponding characteristic (d=0.3) in FIG. 3c. Each path has a particular angle θ from the vertical when it reaches the ground. The path is modeled in reverse: sound leaves the ground at angle $\theta_0$, as shown below. It is assumed that the sound travels straight in layer 64 with characteristic d0. At the interface between layers 64 and 66 (with characteristics d0 and d1), Snell's law is applied using ($n_0 \sin\theta_0 = n_1 \sin\theta_1$) to determine the angle $\theta_1$ at which the sound propagates in layer 66. Values n0 and n1 are inversely proportional to the speed of sound in each layer; the speed of sound is proportional to the square root of temperature. Snell's law is applied again at the interface between layers 66 and 68 and at the interface between layers 68 and 70. Four layers are employed for the explanation herein. In a tested exemplary case, several tens of layers are employed to improve resolution. Then, given each layer d's traverse angle $\theta_d$ and thickness $a_d$, we geometrically compute the distance $r_d$ along that path within each layer: $r_d = a_d$ secant $\theta_d$. This assumes sound travels straight within each layer as an example which is easy to explain and compute. To achieve greater accuracy, in an exemplary embodiment, a curved-path method such as Runga-Kutta is employed to obtain a better estimate of the initial and final angles within each layer. The length of the corresponding curved segment within each layer is then computed.

The distance for each layer goes into matrix A at the element corresponding to that layer and that path. We compute values for other paths by starting with other values of $\theta_0$.

Figure 3D:
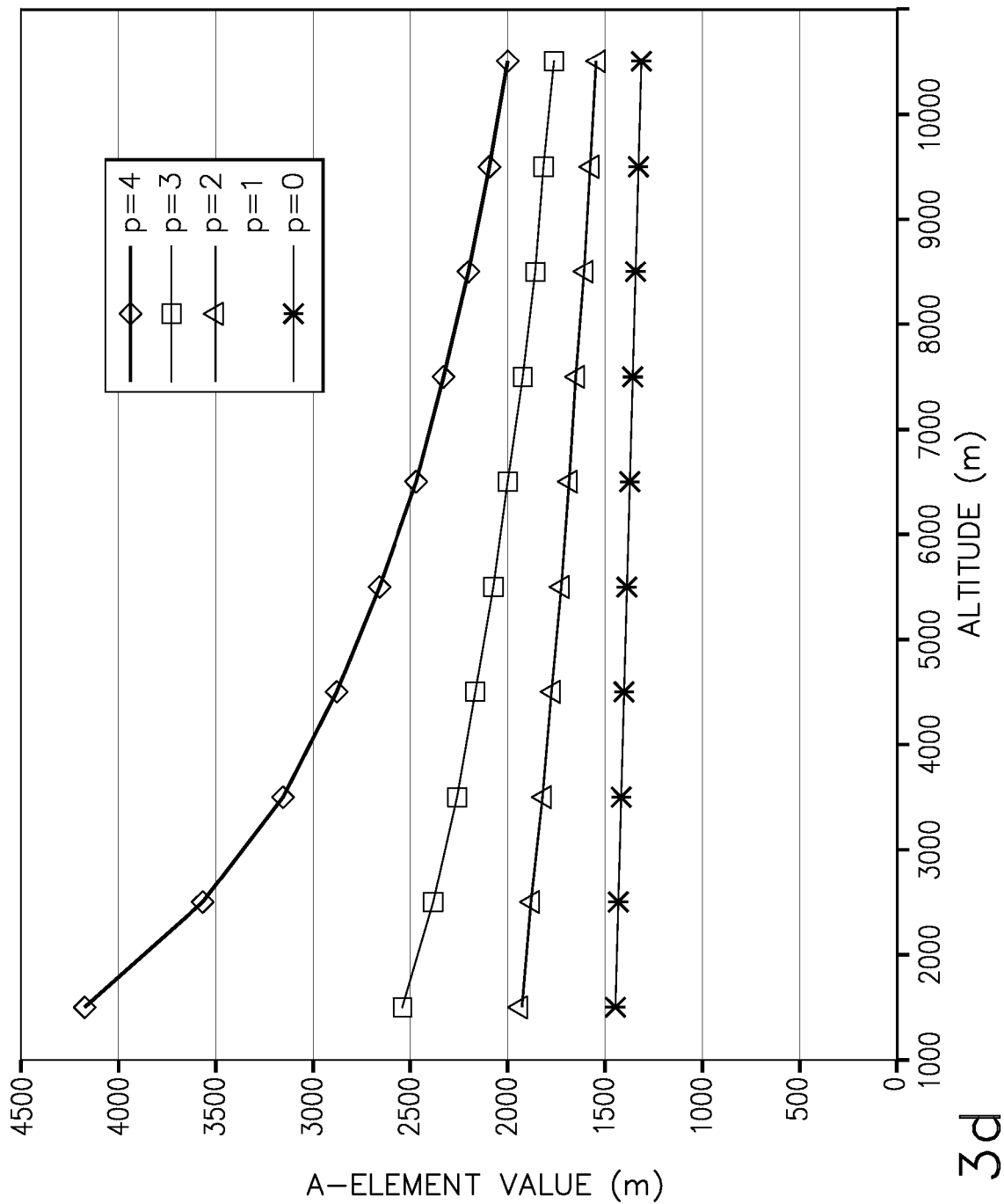
FIG. 3d is a plot of data for multiple layers in an exemplary model employing the present invention.

The plot in FIG. 3d shows numerical values of elements in matrix A for five paths (p=0.4) and ten altitude layers, from zero to 10,000 meters. The values plotted are the distances sound travels in its path through each 1000-meter layer of altitude.

In the numerical model employed in the exemplary embodiment, a ground-level air temperature of 293 Kelvins is assumed. That temperature is defined as having n=1. A still-air lapse rate of −6.5 Kelvins per 1000 meters of altitude gain is modeled, so the temperature at 10,000 meters was 228 Kelvins, or n=1.134. The upper curve (path p=4) started at θ=1.329 radians from vertical near the ground and finished at θ=1.047 radians from vertical above 9000 meters. The lower curve (path p=0) started at θ=0.805 radians and finished at θ=0.710 radians.

Figure 3E:
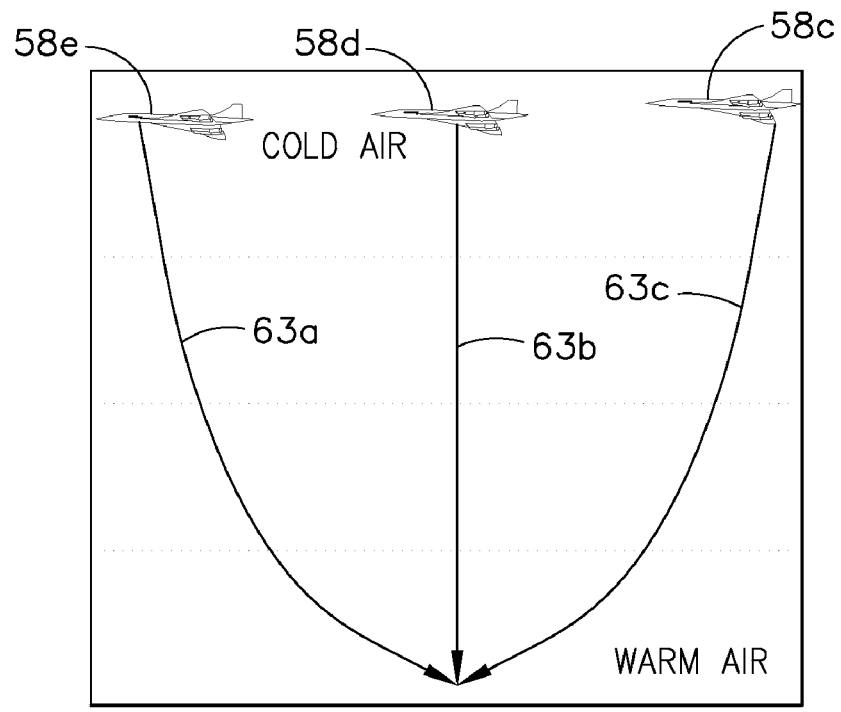
FIG. 3e is a schematic view of various sound paths from an overflying sound source before and after passing over a measuring microphone.
Figure 3F:
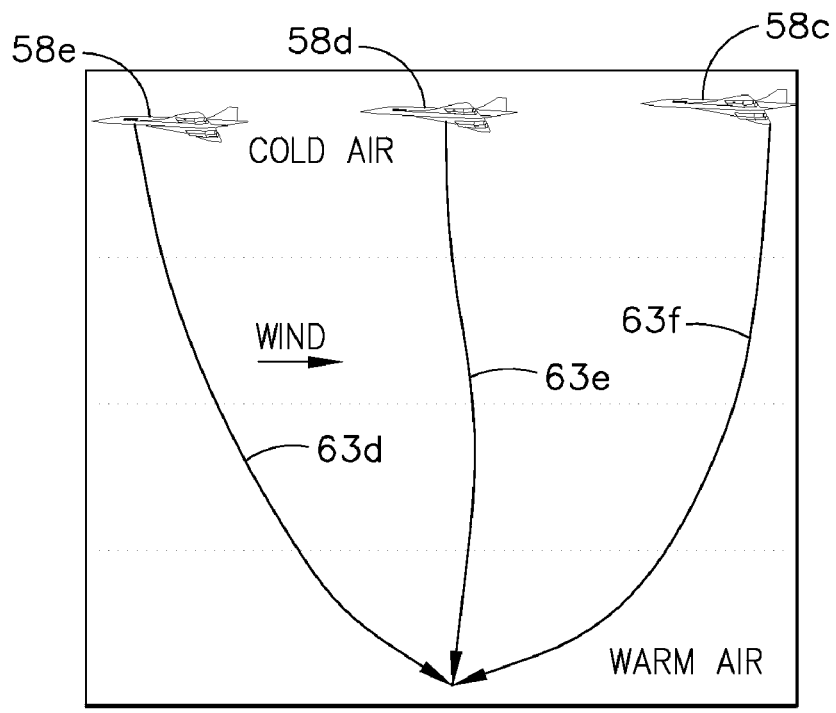
FIG. 3f is a schematic view of the sound paths of FIG. 3e perturbed by an exemplary wind.

In FIG. 3e, paths 63a, 63b and 63c at different intervals in the overflight of the airplane are bent by temperature in a symmetrical pattern about microphone. However, as shown in FIG. 3f, paths 63d, 63e and 63f bent by wind and temperature are asymmetrical. (All curvatures exaggerated for clarity.)

It is possible to solve the simultaneous equations with only a series of acoustic measurements, fitting the data to appropriate curves of frequency and amplitude to estimate the time, altitude, and speed of the airplane producing the sound. However, an exemplary embodiment uses measurements of the airplane's location (x, y, z) as a function of time so the source of sound waves at each moment can be estimated more precisely. A further refinement to this exemplary embodiment computes the vector difference between the airplane's true airspeed and its true ground speed. This vector difference equals the wind velocity at the airplane's altitude, as a parameter for defining boundary conditions of the wind estimate. This vector difference is used in prior art to estimate wind speed at aircraft altitude, but is not used in conjunction with any means to estimate winds at intermediate altitudes. Additionally, the exemplary embodiment uses measurements of wind speed at the surface, as a parameter for defining boundary conditions. Finally, the exemplary embodiment uses temperature measurements at the surface, at the airplane, or both, to define boundary conditions for speed-of-sound estimates.

The previous description of an embodiment of the invention relies on measuring arrival times of sound, but the more easily measured quantity is sound frequency. Frequency of the sound arriving at the microphone varies when the amount of delay in arriving sound waves changes from one sample to the next. This changing delay occurs due to variation in the path length through various winds as well as variations due to the aircraft motion.

Figure 3G:
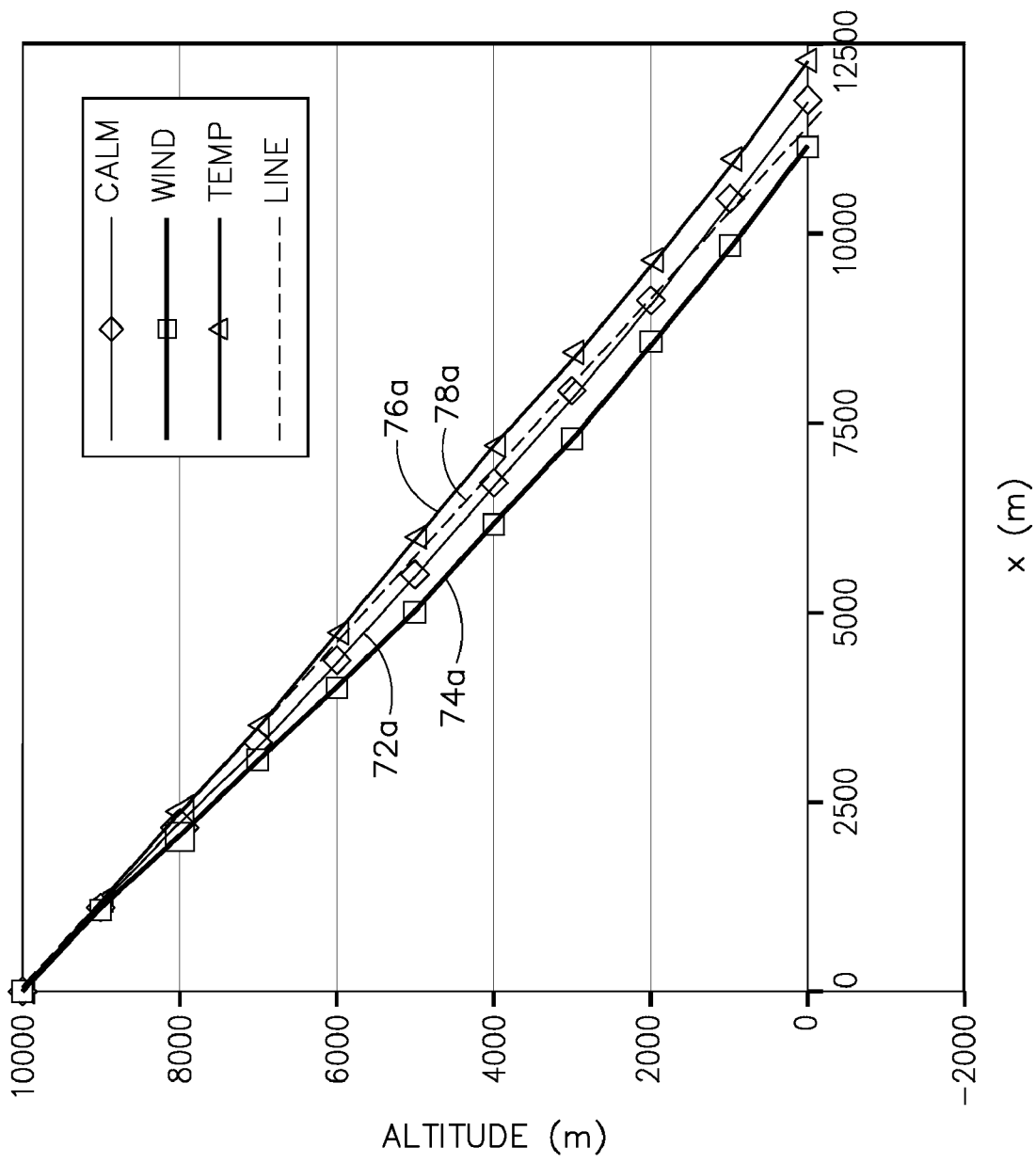
FIG. 3g is a plot of data for acoustic paths with varying atmospheric profiles of wind and temperature.
Figure 3H:
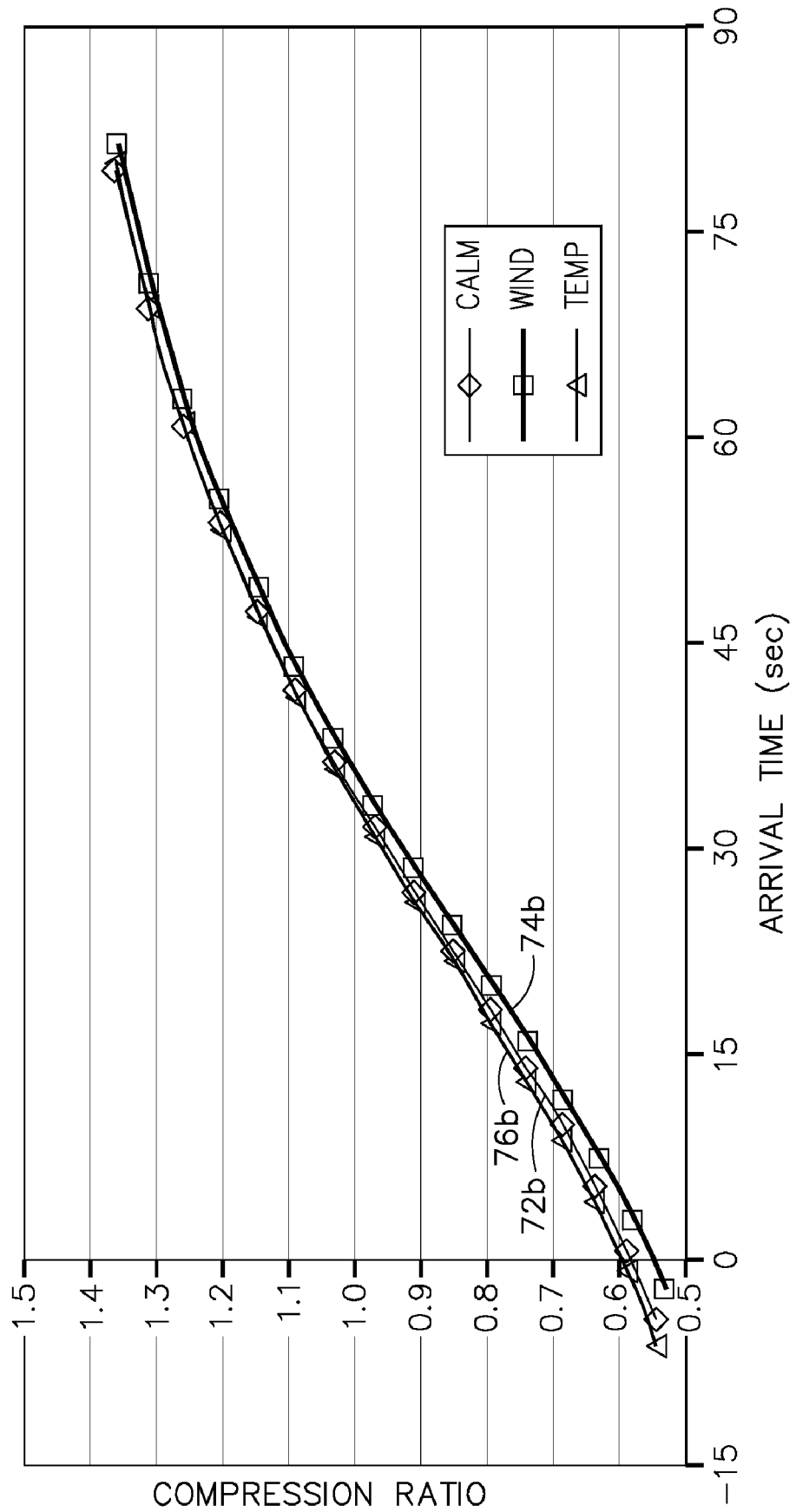
FIG. 3h is a plot of data for acoustic compression ratio (Doppler shift) for various atmospheric profiles.

An alternative embodiment of the invention disclosed herein has modeled this effect using a 10-layer model of the atmosphere. Based on user-selected winds and temperatures at each altitude, the model computes acoustic paths from 10,000 meter altitude to sea level, the emission time and arrival time for sounds emitted by an airplane flying at a user-selected speed, and the apparent Doppler shift for the arriving sounds. FIG. 3g shows 2D paths (altitude vs. x) for three atmosphere models: a first path 72a is calm with a typical thermal lapse rate, a second path 74a has 30 m/s mid-altitude winds tapering to weaker winds at the surface and at 10,000 meters, and a third path 76a has an anomalously warm layer of air from 9000 meters to 5000 meters. For comparison, a straight path 78a is shown as dashed line. FIG. 3h shows the Doppler shift vs. time for these three cases, calm as path 72b, path 74b with winds and path 76b with a temperature impacted layer. Though the three curves have similar shapes, they differ in significant ways. To verify these changes, 1000 different simulated atmospheres were generated (using exemplary statistical data for winds and temperatures over Chicago in January) and the exemplary model in the described embodiment of the invention was employed to predict Doppler curves for each of them. A quadratic discriminant function is employed to assign each Doppler curve to a predetermined class of weather. The Doppler curves carry enough information to resolve winds and temperatures.

Doppler is also useful for detecting turbulence. The size of turbulence cells is typically a few hundred meters or smaller. An airplane can fly over one in a few seconds at most, so turbulence will delay some sound paths and accelerate others quite nearby. Turbulence will therefore appear as short-period humps and valleys in the Doppler curve, so it can be detected by applying a high-pass filter to the Doppler curve. Because turbulence usually has a vertical wind component, its effect on the delay of near-vertical sound waves is much stronger than the effect of horizontal wind. This makes acoustic Doppler a particularly sensitive means to detect and measure turbulence.

Figure 5:
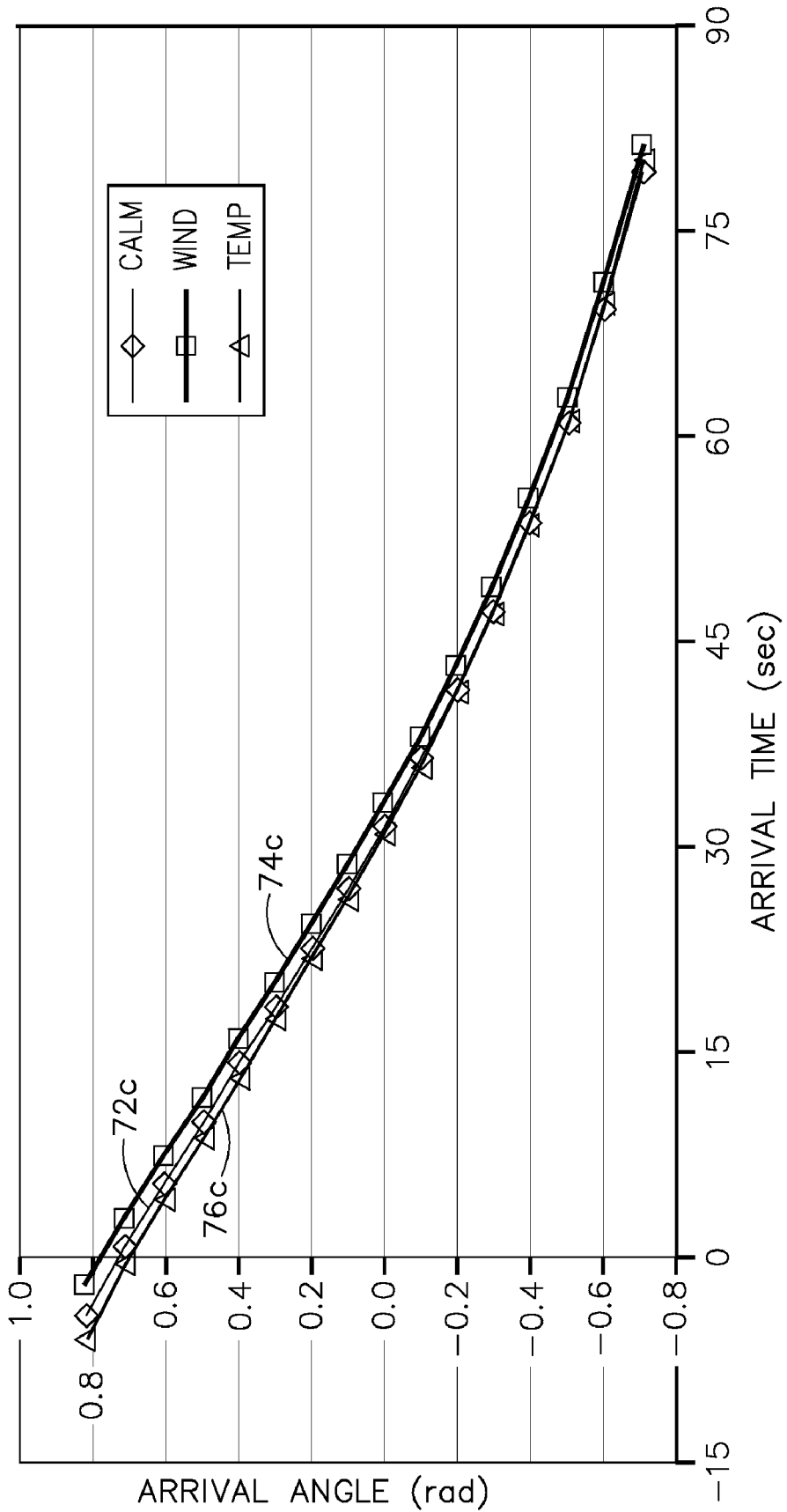
FIG. 5 is a plot of data for acoustic arrival angle at the microphone for various atmospheric profiles.

In addition to measuring Doppler shift, the sound waves' arrival angle is measured at the ground for certain embodiments. The arrival angle is steep for a sound path that has been refracted toward the ground and shallow for a path that has been refracted away from the ground. Arrival angle can be measured with a directional microphone, e.g. a phased array as will be described in greater detail subsequently. Arrival angle results for our model are shown in FIG. 5 with the calm 72c, wind impacted 74c and temperature impacted 76c curves and, as for Doppler, the curves have measurable differences which are employed in the calculations described herein.

Another observable quantity used in certain embodiments is acoustic attenuation, i.e. the decrease in sound intensity with distance along the sound's path. For a given distance from airplane to microphone, attenuation is less for shorter (straighter) paths and greater for longer (bent) paths. Attenuation can be estimated either by direct measurement of sound amplitude or by comparison of the acoustic power at high and low frequencies. A detailed mathematical treatment of the energy ratio method is available in Kak and Slaney, Principles of Computerized Tomographic Imaging, IEEE Press, 1988, pp. 154-155.

Attenuation is another sensitive indicator of turbulence. Turbulence is often caused by cells of warmer or cooler air. A convex cell of warm air affects sound the way a concave lens affects light: it makes the waves diverge. That reduces the sound intensity for sound that traverses a warm cell. (The reverse is true: convex cold cells make sound converge. This increases intensity over short distances, but reduces it for points beyond the focal distance.) Turbulence will therefore appear as short-period humps and valleys in the intensity of sound. These can be detected via a high-pass filter.

Figure 4A:
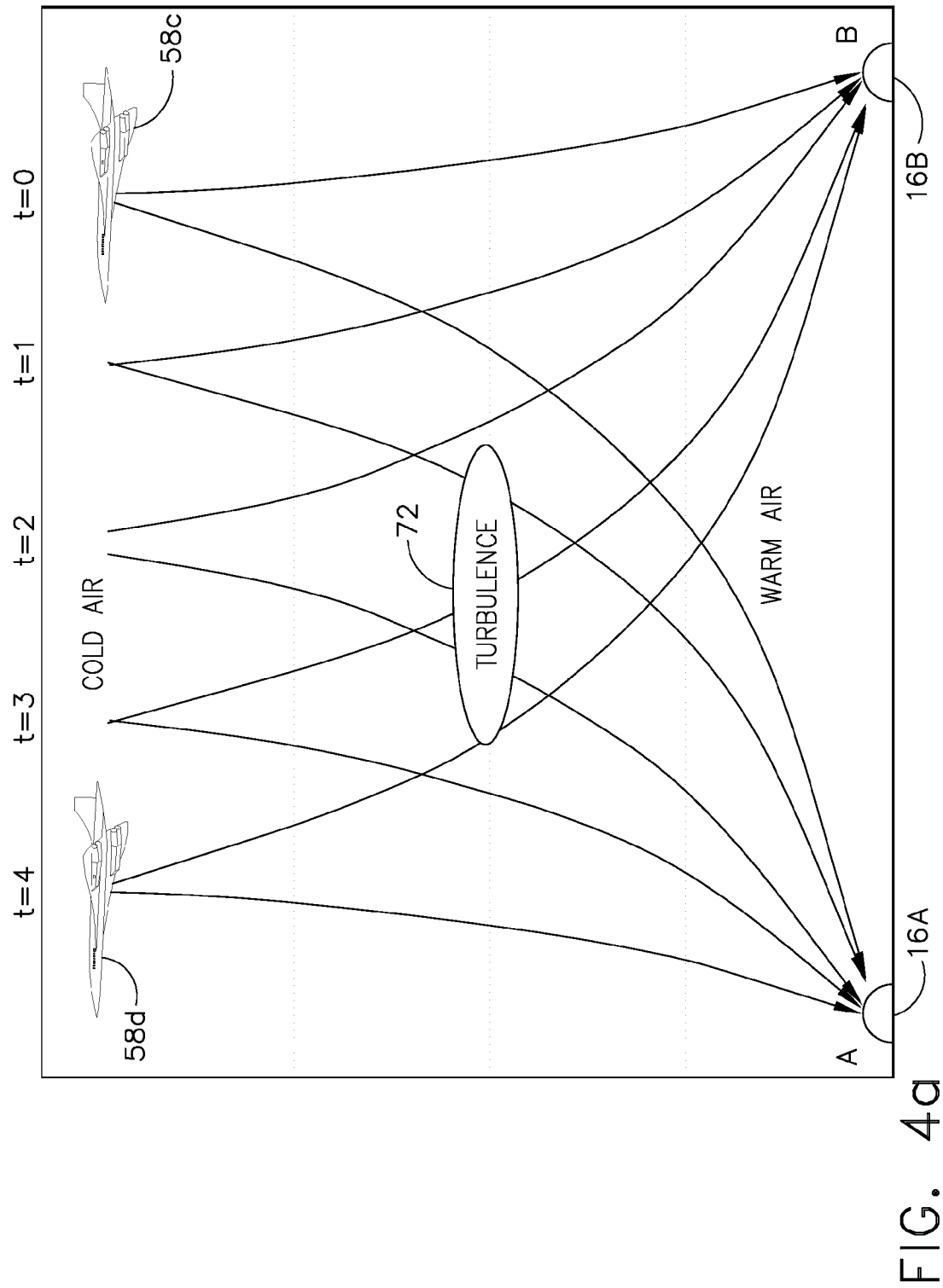
FIG. 4a is a view of various paths from an overflying sound source to two microphones with an intersected turbulent region.

In FIG. 4a microphones 16a and 16b are arrayed on the ground. An airplane 58 flies over from a first position designated 58c to a final position designated 58d. Sound reaches the two microphones by various paths represented at discrete time intervals t=0 to t=4. Along some paths, the sound traverses a region of turbulence 72 (shown here with a typical shape—most turbulent patches are elongated horizontally). The turbulence is detectable on the ground by rapid fluctuations in amplitude and frequency of the sound. Specific isolation of the indicative fluctuations is accomplished using a high pass filter in the sound detection system. For microphone 16a, turbulent effects are observed along the path originating at time t=1 and all subsequent paths up to about time 2.5 (interpolating between t=2 and 3). For microphone 16b, turbulent effects are heard along paths from about time 2.5 to time 4. Using knowledge of the anticipated path profiles (based on temperature and wind profiles), one end of the turbulent region is located at the point where the calculated path to microphone 16a at time (t=1) intersects path to microphone 16b at (t=2.5). The other end of the turbulent region is located at the point where the calculated path to microphone 16a at time (t=2.5) intersects path to microphone 16b at time (t=4).

Figure 4B:
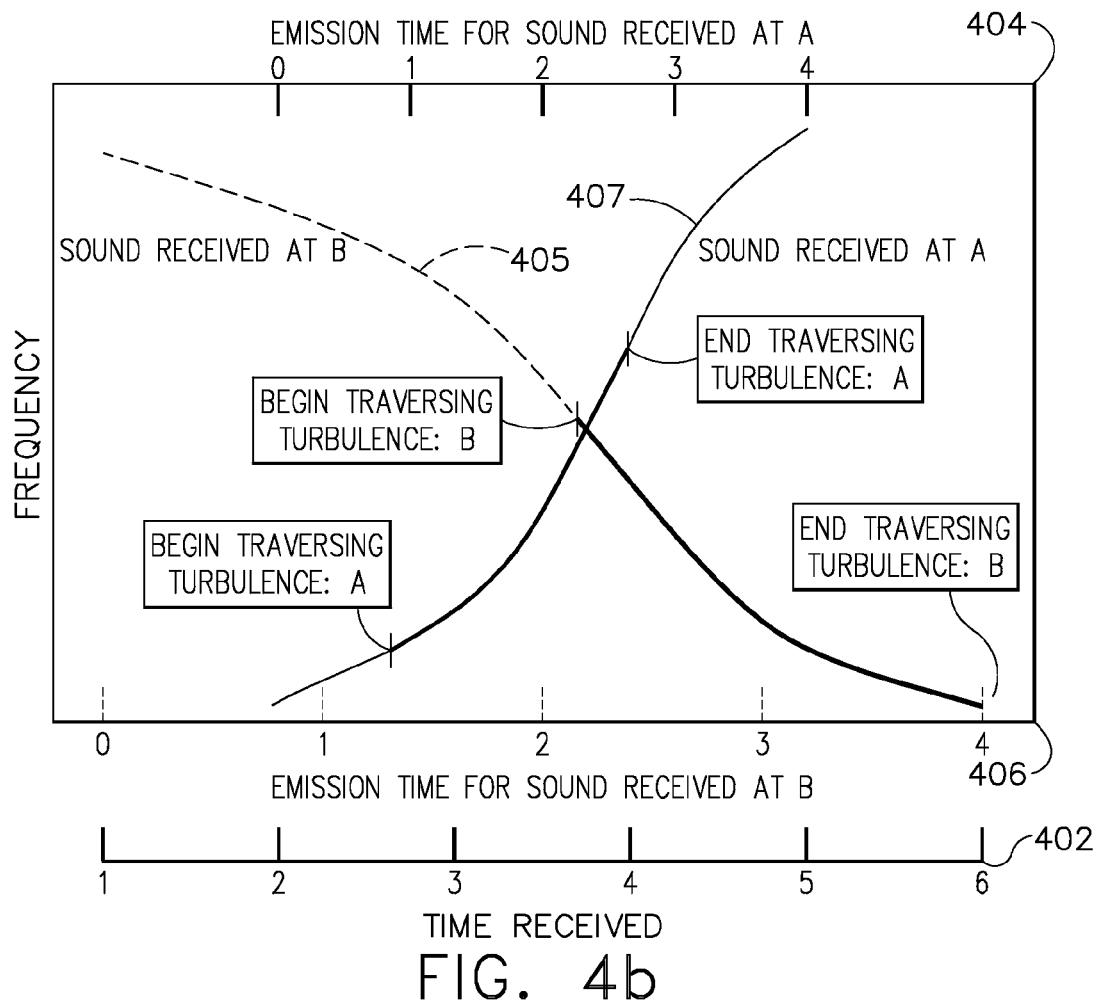

As shown in FIG. 4b, the sound arriving at microphones A and B is emitted earlier than it is received. The interval during which sound arrives at A is shorter than the interval over which sound is emitted. The interval during which sound arrives at B is longer than the interval over which it is emitted. This is due to the airplane's motion. During the interval shown, the airplane is moving away from B and toward A. FIG. 4b has three horizontal scales of time, spanning times from t=0 to t=6. The "time received" scale 402 is the same for microphones A and B, but the emission time scales, 404 for sounds received at microphone A and 406 for sound received at microphone B, differ. For example, sound 405 reaching microphone B at time 4 is emitted from the aircraft at about time 2.3. Similarly, sound 407 reaching microphone A at time 4 was emitted at about time 2.6

Figure 4C:
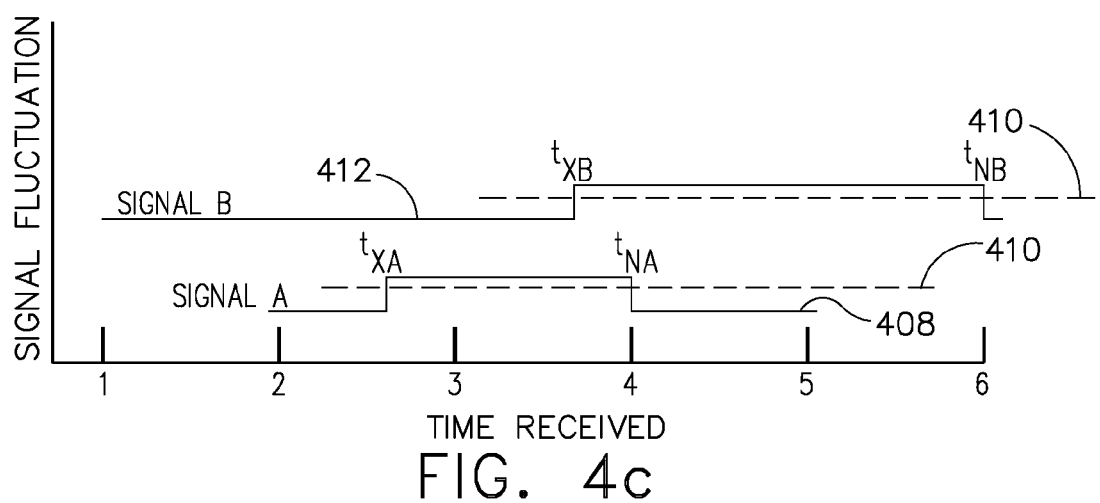
FIG. 4c is representative traces showing signal fluctuation created by the turbulent zone for the sounds arriving in FIG. 4b.

At the receiving microphones, a high-pass filter is applied to the acoustic measurement to enhance the short-term fluctuations. For the embodiment shown, frequency is the measured variable while in alternative embodiments amplitude is measured. The signal is rectified and smoothed to give a low value when the sound traverses non-turbulent air and a high value when the sound traverses turbulent air, as shown by the traces in FIG. 4c. A microphone-dependent threshold value is used to distinguish high and low values. As shown, fluctuations 408 in signal A exceed the threshold 410 at $t=t_{XA}$ and return to normal at $t=t_{NA}$. Fluctuations 412 in signal B exceed the threshold at $t=t_{XB}$ and return to normal at $t=t_{NB}$.

To locate that end of the turbulent region, the point where the two paths intersect is computed (for two dimensional (2D) paths, as illustrated in FIG. 4a) or where the distance between the two paths is minimal (for three dimensional (3D) paths, as in real applications). Determination of the minimum for exemplary 3D embodiments employs a piecewise computation of closest approach among various line segments in the two paths. This procedure is then repeated using $t_{NA}$ and $t_{NB}$ to locate the other end of the turbulent region.

The procedure described for the exemplary embodiment above is simple, but gives little indication of the intensity of turbulence. In an alternative embodiment, multiple thresholds are used to detect transitions between low and high acoustic fluctuation. The use of multiple thresholds allows the invention to detect and locate regions of strong turbulence (which exceeds the highest threshold) and of moderate or weak turbulence (which exceeds only medium or low thresholds).

In another alternative embodiment, the method of the invention applies various time offsets and time stretching coefficients to delay and stretch the acoustic fluctuation signal at microphone A. This method of the invention adjusts the offset and stretching coefficient to maximize the temporal correlation coefficient of fluctuation signal A with the fluctuation signal at microphone B. Because the correlation is maximized over the whole interval, a more robust alignment of signal A to signal B is obtained than a method based on endpoints alone. This gives a more improved estimate of the location, extent, and strength of the turbulent region based on the increased volume of available data.

With multiple microphones, including some dispersed to the sides of the airplane's ground track, data received is representative of additional geometric orientations with respect to the source of the acoustic spectral data received and improved resolution of the turbulent region can be attained.

Estimates of the wind-induced Doppler shift are more difficult if the frequency of the sounds emitted by the airplane changes in unknown or unpredictable ways. Therefore, the exemplary embodiment uses measurements of the airplane's true airspeed (a source of wind noise), engine turbine rotation rate (a source of machine noise), and/or thrust (an indicator of exhaust turbulence noise), each of which helps refine the estimate of the noise spectrum being produced by the airplane. These measurements from the airplane are downlinked via a communication system such as Aircraft Communication Addressing and Reporting System (ACARS) or Connexion™ by Boeing. An alternative embodiment uses a computational model (either empirical or analytic) of the noise spectrum emitted by the airplane in various downward directions as a function of airspeed, engine speed, and thrust. This helps refine the estimate of the noise spectrum being emitted along the particular path from the airplane to the microphone. Similarly, an embodiment that uses attenuation measurements benefits from measurements of airspeed, turbine speed, and thrust, plus a computational model of noise emitted in each direction from the aircraft.

When the airplane passes nearly straight over the microphone, it is hard to distinguish winds blowing left-to-right (relative to the flight path) from those blowing right-to-left: both wind directions cause the same delay. To resolve this ambiguity, two or more microphones are employed, distributed so that the ground track of a typical aircraft flight will pass at a different distance from each microphone. The use of additional microphones in a small region (for example, a few kilometers on a side) has two additional benefits. First, providing more data points, thereby improving statistical validity of estimated winds, turbulence, and temperatures, and, second, providing data points from sound paths that are horizontally separated, thereby localizing areas where turbulence is detected and providing estimates of horizontal variation in winds and temperatures.

Figure 6A:
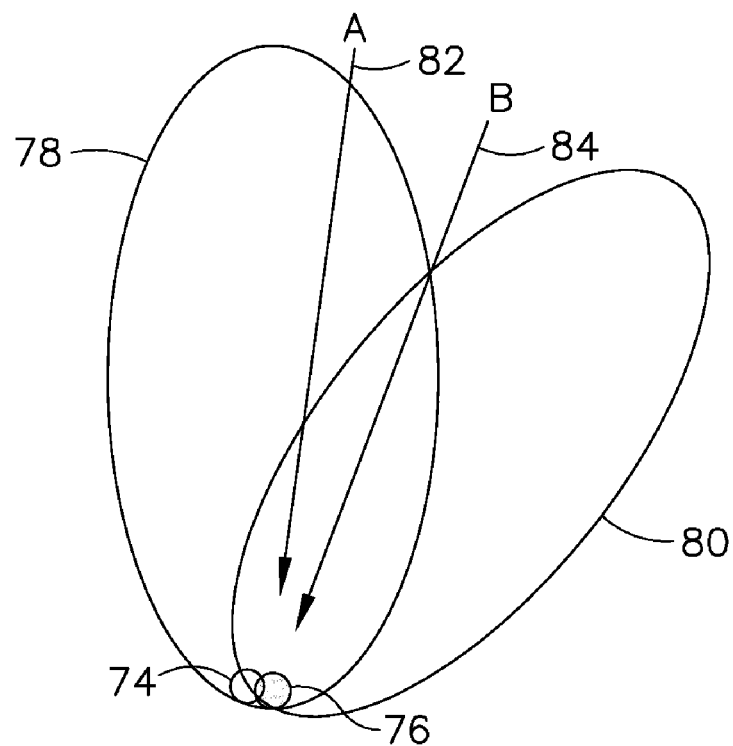
FIG. 6a is a schematic representation of a direction sensing microphone arrangement for determining acoustic arrival angle.

To measure the arrival angle of sound at a microphone, three alternative methods are employed in various embodiments. In a first method, a set of fixed directional microphones, such as cardioid microphones, are oriented in different directions. Then the ratio of acoustic amplitudes measured by the microphones can be indexed to the angular gain of each antenna to indicate the direction of arrival. FIG. 6a shows two microphones 74 and 76 mounted together. The angular gain patterns are indicated by ellipses with pattern 78 associated with microphone 74 and pattern 80 associated with microphone 76. The greatest gain is in the direction of the major axis of the ellipse. Sound arriving from a direction indicated by vector 82 gives a much stronger signal for the left-oriented microphone (76) than for the right-oriented microphone (78). Sound arriving from a direction indicated by vector 84 gives roughly equal signals for the two microphones. Measuring the ratio of acoustic signals gives an accurate indicator of the direction a signal comes from. (More than two microphones can be used to improve precision and resolve ambiguities.)

Figure 6B:
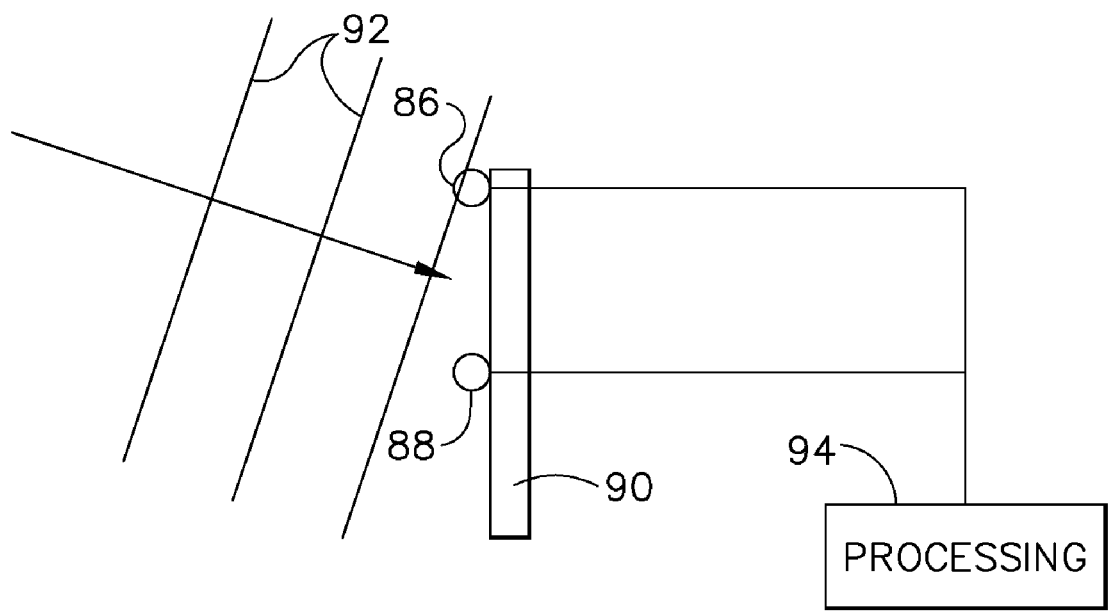
FIG. 6b is a schematic representation of a phased array of microphones for sensing acoustic arrival angle.

In a second method, a phased array of microphones is employed as shown in FIG. 6b. Here, two microphones 86 and 88 mounted on a vertical support 90 receive an acoustic signal arriving as a series of plane waves 92. The waves reach upper microphone 86 earlier than lower microphone 88. The difference in time of arrival depends on the angle of arrival and on the temperature. A processing system 94 is employed to measure the time difference and the temperature, and then compute the arrival angle 96. Separation of the microphones horizontally on a support structure is employed in alternative embodiments to the vertical separation for the embodiment shown.

A third method employs a single directional microphone that scans (typically in a "coning" pattern) to measure the direction of the strongest signal.

Finally, it must be noted that sounds from an airplane, or even from loud objects on the ground, can propagate upward to a microphone carried by a weather balloon, and these sounds can be used to estimate winds, temperatures, and turbulence at intervening altitudes. This would provide more mid-altitude weather data than current art: today, a balloon only collects mid-altitude data during its ascent. Therefore, an alternative embodiment of the invention provides the microphone aloft with onboard calculation or telemetry of the data to the ground for calculation.

Figure 6C:
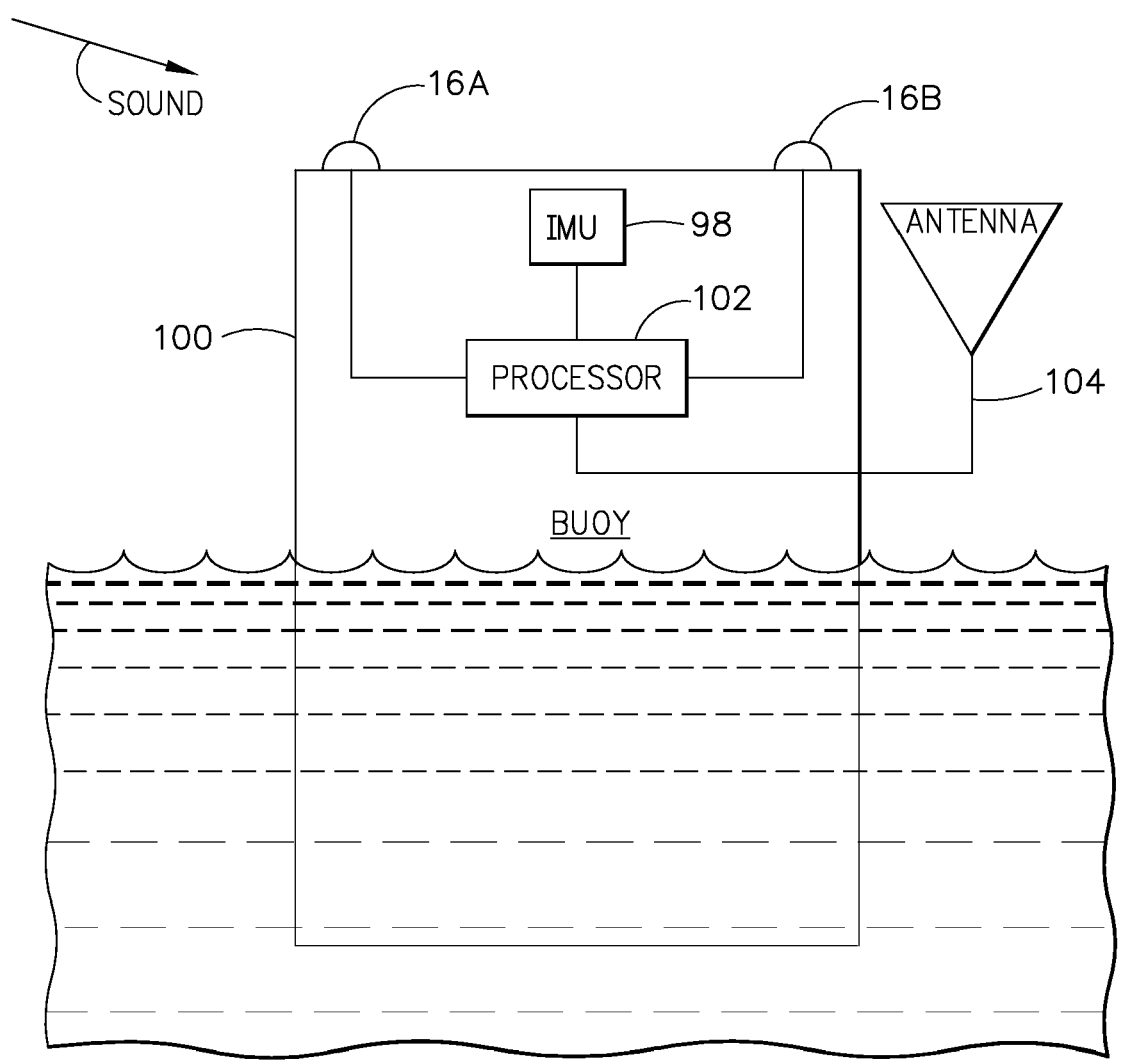

The simplicity of the measurement equipment and the passive nature of using existing sound sources such as aircraft permits the present invention to be used in such scenarios as microphones mounted on buoys for conducting measurements over water. For arrival angle information using models such as those described, for a buoy or other unsteady platform, a device capable of measuring acceleration and/or tilt angles due to the buoy's rocking in waves, and a device capable of computing an appropriate correction to the Doppler shift and arrival angle to cancel the effect of the buoy's motion is employed. The elements of an exemplary buoy mounted system are shown in FIG. 6c.

The key addition, relative to fixed embodiments, is the inertial measurement unit (IMU) 98 mounted on buoy 100. The aircraft sound arrives at microphones 16A and 16B, which are mounted on the buoy. The microphones and associated electronics measure the frequency, amplitude, and arrival angle of the arriving sound. However, these quantities may be distorted by motion of the buoy in the water. For example, if the buoy is surging to the right when sound arrives from the left, then the measured frequency will be Doppler shifted to a lower frequency than the actual frequency. Likewise, if the buoy tips to the left, then the measured arrival angle for any sound arriving from the left will be higher than the actual arrival angle.

The IMU measures accelerations and rotations of the buoy. The processor 102 uses data from the IMU to correct the measured acoustic parameters, e.g. subtracting the buoy's off-nominal attitude from the measured acoustic arrival angle to compute the actual arrival angle. The processor then transmits the corrected data to users via the radio antenna 104 and associated electronics.

It will be apparent to those skilled in the art that a meteorological buoy usually contains a great deal more equipment than shown here, e.g. thermometers, rain gages, anemometers, GPS receivers, and others. It will also be apparent that the elements of this embodiment can be used to make acoustic measurements using other platforms whose location and attitude may continually change, such as ships, balloons, or flexible towers.

Additionally, the simplicity of the measurement system can be used to provide a low cost network of measurement points with either centralized or distributed computing systems to allow linking data from each of many airplanes to data from microphones that the airplane is currently close to, from among many microphones around the world. Significant geographic coverage for profiling atmospheric conditions can be provided by the network.

Figure 7:
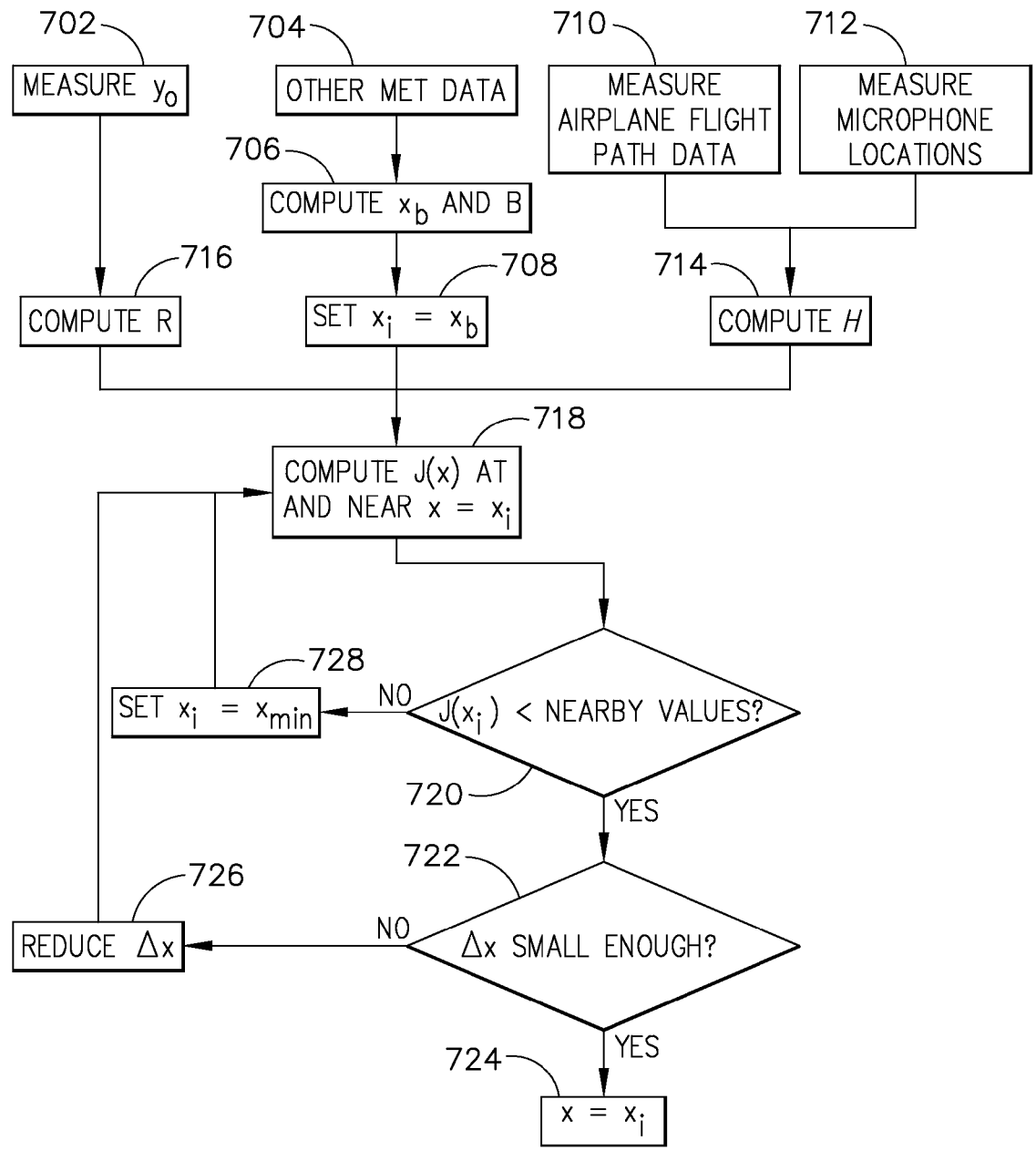
FIG. 7 is a flow chart of components of the calculation engine for minimizing the cost function to obtain solutions for the simultaneous equations for an exemplary embodiment of the invention.

Several computational approaches can be used to transform measurements of sound into estimated atmospheric profiles. The approach that is most versatile and most accepted in the meteorology community is based on variational analysis. FIG. 7 demonstrates a variance analysis employed in an embodiment of the present invention, as will be described subsequently. As a general synopsis, a vector, x, contains values of atmospheric properties to be estimated. An example of one property contained in x might be the temperature at 25,000 feet, latitude 30 degrees, longitude 50 degrees east. Another value in x might be the eastward component of wind at the same location. The values in x are varied to minimize a cost function given by:

$$J(x) = \tfrac{1}{2}(x-x_b)^T B^{-1}(x-x_b) + \tfrac{1}{2}(Hx-y_0)^T R^{-1}(Hx-y_0)$$

where J is the cost to be minimized, $x_b$ is a prior estimate of x based on other sensors or models, B is a matrix of weights based on confidence in (and covariance of) various values in $x_b$, H is a "forward model" that transforms a given vector of atmospheric properties into a vector of observable quantities such as sound frequency at various times, $y_0$ is the vector of quantities actually observed, and R is a matrix of weights based on confidence in (and covariance of) various values of Hx and of $y_0$. For example, consider a case derived from the one shown in FIG. 3a. For the example shown, the vector of observations, $y_0$, contains five elements, one for each measurement of acoustic frequency at times corresponding to paths p=0 to p=4. The vector (Hx−$y_0$) therefore contains differences $\Delta f_i$ between predicted frequencies, Hx, and measured frequencies $y_0$. For any physical measurement, there is some background noise. The confidence in frequency measurements depends on the signal-to-noise ratio at the time of measurement. Elements of matrix R are computed by using a nominal atmosphere model (including boundary conditions, if available) and the measured aircraft flight path vs. time. Diagonal elements of R are large for measurements where high amplitude (and therefore high signal-to-noise) is expected, e.g. p=0, and small where low amplitude is expected, e.g. p=4. This means errors in high-quality frequency measurements have a large effect on J(x), while errors in low-quality measurements have a small effect. The particular values in R depend on the microphone and the filters or processing algorithms used to estimate frequency from the measurements, as these factors affect the noise tolerance of the estimate.

An example matrix R is shown in FIG. 8a, along with vector (Hx−$y_0$). As described above, the diagonal elements of R are large for paths where the expected amplitude is large, e.g. along path p=0. This gives more weight to frequency errors such as $\Delta f_0$ where the expected quality of the frequency measurement is good, and less weight where the expected quality is poor.

In an exemplary embodiment, amplitude measurements are employed in addition to frequencies. For an exemplary case, the vector of observations, y0, contains ten elements. Five are measurements of acoustic frequency at times corresponding to paths p=0 to p=4. The other five elements are measurements of acoustic amplitude at the same times. Elements of matrix R are computed by using a nominal atmosphere model (including boundary conditions, if available) and the measured aircraft flight path vs. time. Diagonal elements corresponding to measured frequency are large for measurements where high amplitude is expected. In addition, non-diagonal elements of R add more weight to frequency measurements when the actual amplitude is greater than expected and reduce the weight when amplitude is smaller than expected. This means the actual quality of frequency measurements is used to increase or decrease the importance of each measurement in computing J(x).

An example matrix R for the embodiment described above is shown in FIG. 8b, along with vector (Hx−$y_0$). The diagonal elements of R are large for paths where the expected amplitude is large, e.g. along path p=0. This is true both in the upper left quadrant, where errors deal with frequency, and in the lower right quadrant, where errors deal with amplitude. In addition, elements in the upper right quadrant give more weight to frequency errors when the measurement amplitude is stronger than predicted. The most extra weight is given to path p=4, where modest increases in amplitude ($\Delta A_4$) increase the signal-to-noise ratio enough to give greatly increased confidence in the measured frequency error ($\Delta f_4$). Zeros in the lower left quadrant show that measured frequency has no effect on confidence in measured amplitude.

Note that the forward model H used in each case depends on the trajectory of the airplane and the locations of the microphones used for the acoustic measurements. Examples of the forward model, H are present in the previously described data results for FIGS. 3h and 5. The software that generated FIG. 3h (acoustic compression ratio, also known as inverse Doppler shift) used ten atmosphere layers and a series of aircraft positions (10,000 meter altitude, various horizontal positions computed as a function of time and the aircraft speed). Using a vector x that includes temperature and east-west wind in each layer, this model H uses Snell's law to propagate acoustic signals across each inter-layer boundary from the aircraft to the microphone. It computes the total transit time along each path, using the path length in each layer and the speed of sound determined by temperature and wind speed in that layer. It then computes the compression ratio for each acoustic sample as the ratio of the (difference in arrival times for two adjacent samples) divided by (difference in emission times for the same samples). For use in the cost equation, H divides the frequency of emitted sound by the compression ratio to get the predicted frequency $Hx_i$ for each sample $x_i$ (as discussed below with respect to FIG. 7) from which we subtract the measured frequency $y_i$ to get one error component, $\Delta f_i$. In an exemplary embodiment, H does not treat the aircraft emission as a single frequency; it instead uses a model of the acoustic spectrum emitted by the aircraft and corrects this spectrum for frequency-dependent attenuation along each path, then applies the acoustic compression ratio to the corrected spectrum to estimate the received spectrum. In this embodiment, $Hx_i$ is a spectrum vector (rather than a frequency scalar, as in the prior embodiment), as is each measurement $y_i$.

Another example of H is the software that generated FIG. 5 (arrival angle). It also uses ten atmosphere layers, the series of aircraft positions, and Snell's law. Rather than acoustic compression, this H computes the arrival angle $Hx_i$ for each acoustic sample. In the cost equation, the measured arrival angle $y_i$ is subtracted from each $Hx_i$.

In demonstrated embodiments, H and y include at least two, and preferably three, of frequency, amplitude, and arrival angle.

In most prior art, values in x are defined only as a function of altitude, not horizontal location. This approach to minimize J(x) is called one dimensional variation (1Dvar). It is suitable for measuring broad-scale weather characteristics, such as steady-state winds over relatively smooth terrain.

The present invention can be used to estimate x where values in x are a function of all three spatial coordinates. (An example is a case where x includes an estimate of turbulence at various locations. Turbulence can be quite localized, especially near mountains.) This approach is called three dimensional variation (3Dvar). The use of 1Dvar for meteorological measurements is well known in prior art. The use of 3Dvar for acoustic meteorological measurements is novel to the present invention and created based on the ability of embodiments of the invention to measure acoustic phenomena at multiple locations.

Returning to FIG. 7 as an implementation provided in one embodiment, the sound data $y_0$ is measured 702. Other meteorological data is measured or applied 704 from a known database using location of the measurement for determination. The $x_b$ and B matrix of weights are determined 706 based on this meteorological data and the initial iteration $x_i$ is set to $x_b$ 708.

Additionally, the airplane flight path data which may include in addition to location and velocity such elements as weight, engine speed, thrust or other parameters for characterization of the sound emitted is provided 710 and the microphone locations are determined 712 for computation of the forward model H 714. These may include the vector difference in true airspeed and true ground speed of the aircraft as a wind velocity vector that is applied as an upper boundary condition.

R is computed as a weighting matrix 716 based on H and $y_0$ providing the last of the elements of the cost function J discussed above. J(x) is then calculated near x at the initial iteration value, $x_i$, 718. If $J(x_i)$ is less than nearby values 720 then a determination is made if $\Delta x$ is small enough 722 where $\Delta x$ is the amount by which x is varied about $x_i$. If so, then the solution of J(x) is complete and $x=x_i$ 724. If not, then $\Delta x$ is reduced 726 and J(x) is computed again. If in step 720 $J(x_i)$ was not less than nearby values, $x_i$ is set to a minimum value $x_{min}$ and J(x) is computed again at step 720.

Since variational analysis is essentially a gradient descent through the space of J(x), the value of x with the lowest J(x) value is selected as the starting point for the next iteration. $x_{min}$ is the value of x that gives the lowest cost J(x) when x varies about $x_i$ by $\pm\Delta x$.

It should be noted, for the embodiments described herein, that $x_i \pm \Delta x$ does not mean simply $x_i + \Delta x$ and $x_i - \Delta x$. Rather, it means $x_i$ varied in the positive and negative direction for each dimension of vector x, with the amount of variation in each direction specified by $\Delta x$. Thus, if x has three elements, $x_i \pm \Delta x$ includes six values of x.

Having now described the invention in detail as required by the patent statutes, those skilled in the art will recognize modifications and substitutions to the specific embodiments disclosed herein. Such modifications are within the scope and intent of the present invention as defined in the following claims.

What is claimed is:

1. A method for characterizing atmospheric conditions comprising the steps of
    gathering acoustic spectral characteristics of an atmosphere with known properties in each of a plurality of layers;
    using said acoustic spectral characteristics to train a discriminant function for discriminating among various atmospheric conditions;
    collecting actual acoustic spectral characteristics created by a sound source; and,
    using the discriminant function to identify a current atmospheric condition.

2. A method as defined in claim 1 wherein gathering spectral characteristics is accomplished using simulated atmospheric properties.

3. A method as defined in claim 1 wherein gathering of spectral characteristics is accomplished by measuring sound emitted by a plurality of aircraft traversing the atmosphere.

4. A method as defined in claim 1 wherein the step of collecting actual spectral characteristics is accomplished by measuring sound emitted by an aircraft traversing the atmosphere.

5. A method as defined in claim 1 wherein the step of using the discriminant function to identify a current atmospheric condition provides an initial vector as an iteration value for minimizing a cost function using collected actual spectral characteristics.

6. A system for characterizing atmospheric conditions comprising:
- means for collecting current spectral characteristics of a sound source traversing the atmosphere;
- a computer having
  - means for storing known spectral characteristics of an atmosphere with known properties in each of a plurality of layers;
  - means for training a discriminant function for discriminating among various atmospheric conditions based on said stored spectral characteristics; and
- means responsive to the collecting means for applying the discriminant function to the current spectral characteristics to identify a current atmospheric condition.

* * * * *